United States Patent [19]

Sekmakas et al.

[11] Patent Number: 4,599,417
[45] Date of Patent: Jul. 8, 1986

[54] UREIDO-FUNCTIONAL ADHESION PROMOTING AMIDE MONOMERS

[75] Inventors: Kazys Sekmakas, Des Plaines; Raj Shah, Schaumburg, both of Ill.

[73] Assignee: DeSoto, Inc., Des Plaines, Ill.

[21] Appl. No.: 668,156

[22] Filed: Nov. 5, 1984

[51] Int. Cl.$^4$ .................. C07D 233/30; C07D 239/02
[52] U.S. Cl. .................................. 544/316; 526/263; 548/320
[58] Field of Search ......................... 544/316; 548/320

[56] References Cited

U.S. PATENT DOCUMENTS

| | | | |
|---|---|---|---|
| 2,980,652 | 4/1961 | Melamed et al. | 544/316 |
| 3,356,653 | 12/1967 | Sekmakas | 548/320 |
| 4,314,067 | 2/1982 | Herman et al. | 544/316 |

Primary Examiner—Harry Wong, Jr.
Attorney, Agent, or Firm—Dressler, Goldsmith, Shore, Sutker & Milnamow

[57] ABSTRACT

Ureido-functional ethylenically unsaturated copolymerizable amide monomers are disclosed which are the adduct formed by reacting an aminoalkyl alkylene urea, preferably aminoethyl ethylene urea, with substantially a stoichiometric amount, based on the amine functionality present, of a maleic anhydride compound in solution in N-methyl pyrollidone. The reaction is carried out at a temperature in the range of 80° C. to 130° C. to form an unsaturated carboxyl-functional amide. To provide amide monomers which are particularly useful for improving the adhesion of aqueous emulsion copolymer used to form latex paints, the carboxyl functionality in the amide is consumed by esterification with an epoxide, such as propylene oxide, to provide an acid value of less than 10.

3 Claims, No Drawings

UREIDO-FUNCTIONAL ADHESION PROMOTING AMIDE MONOMERS

DESCRIPTION

1. Technical Field

This invention relates to monoethylenically unsaturated monomers which promote adhesion in polymers and copolymers, and especially in aqueous emulsion copolymer latices which are in common use to provide latex paints.

2. Background Art

Many monoethylenically unsaturated monomers which promote adhesion are known, there being a considerable literature in this subject matter illustrated by U.S. Pat. No. 3,356,653 to K. Sekmakas. These monomers are now in common use, especially in aqueous emulsion copolymers where they improve the adhesion of latex paints to the various substrates to which such paints must adhere. It is advantageous to employ ureido-functional monomers based on aminoethyl ethylene urea, as illustrated by U.S. Pat. No. 4,319,032 to J. M. Sandri et al., since these provide good wet adhesion. However, these use unsaturated epoxy compounds, like glycidyl methacrylate or allyl glycidyl ether, which introduce difficulty and expense, so it is desired to avoid their use.

One economical possibility is to provide amide monomers based on the previously mentioned aminoethyl ethylene urea and compounds closely related thereto, but this has not previously been possible, so the adhesion-promoting capacity of such products could never be evaluated. If the aminoethyl ethylene urea is mixed with some appropriate carboxylic acid, like maleic acid or anhydride, in the absence of an organic solvent, then the exothermic reaction is uncontrollable and cannot be safely handled. On the other hand, conventional solvents, like xylene or methyl ethyl ketone, cannot be used because a solution never forms. As a result, this possibility has not become a part of the prior art.

DISCLOSURE OF INVENTION

In accordance with this invention, an aminoalkyl alkylene urea, and especially aminoethyl ethylene urea, is reacted with a maleic anhydride compound, a term which includes substitution products thereof which retain the maleic unsaturation and the anhydride group, like a chlorinated maleic anhydride, and this language will be used to define this limited group of compounds herein. The reaction of the invention is carried out in solution in N-methyl pyrollidone at a temperature in the range of 80° C. to 130° C., and the reactants dissolve and adduct with one another to form an ureido-functional amide. This amide is carboxyl-functional and this carboxyl functionally can be retained so that copolymerization forms carboxyl-functional copolymers.

The maleic anhydride will react to the extent used so long as amine functionality remains, but substantially stoichiometric amounts are preferred to consume all the amine functionality. It will be understood that for many purposes a subsequent reaction with epoxides is contemplated, so any remaining amine functionality will be destroyed by reaction with the epoxide.

When the monomer is to be used to form adherent emulsion copolymers for use in latex paints, it is usually necessary to minimize the acidity, and this is easily done by reacting the carboxyl-functional amide monomer with an epoxide which is preferably a monoepoxide to provide a monoethylenically unsaturated monomer in which hydroxy functionality replaces the undesired carboxyl functionality. Polyepoxides will form polyethylenically unsaturated products, and these can also be used, though they are less preferred for emulsion copolymers intended for use in latex paints. The polyepoxides which can be used are preferably diepoxides, especially diglycidyl ethers. The diglycidyl ethers based on bisphenol A are readily available, being known as epoxy resins, and these will illustrate the preferred diepoxides. Epon 828 provides a specific commercial illustration.

Latex paints made from aqueous emulsion copolymers containing from 0.1% to 10%, preferably from 1% to 5%, of the low carboxyl content monoethylenically unsaturated amides of this invention have been found to possess normal gloss and gloss retention, and to possess good to excellent adhesion, as indicated by wet adhesion testing.

As previously indicated, the aminoalkyl alkylene ureas which are used are known compounds and preferably have the amine group in the omega position. The compound of choice, based on its availability, is 2-aminoethyl ethylene urea, but 2-aminoethyl propylene urea is also useful. One can also use 4-aminobutyl ethylene urea and 6-aminohexyl ethylene urea. These aminoalkyl alkylene urea compounds have the following structural formula:

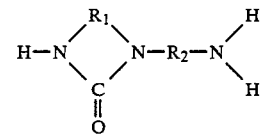

in which $R_1$ is alkylene having 2 or 3 carbon atoms, preferably 2 carbon atoms; and $R_2$ is alkylene having 2 to 10 carbon atoms, preferably 2 to 3 carbon atoms.

Maleic anhydride may be replaced only by its substitution products which retain the maleic unsaturation and the dicarboxylic acid anhydride group. Thus, one or more of the hydrogen atoms in maleic anhydride can be replaced by a methyl group or a halogen, such as chlorine, bromine, iodine or fluorine.

These compounds can be described as having the following structural formula:

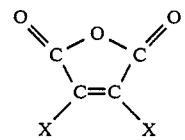

where X is hydrogen, $C_1$-$C_4$ alkyl or halogen. Thus, compounds such as dimethyl maleic anhydride or dichloromaleic anhydride, may be used.

The amide-forming reaction between a primary amine and the dicarboxylic acid anhydride group is well known for amines and anhydrides other than those used herein, and it requires no catalyst. However, the compounds named herein have not previously been reacted. At temperatures of about 80° C., the reaction rate herein becomes acceptable, and it goes faster with increasing temperature. The product becomes progressively more discolored as the reaction temperature increases, so about 130° C. represents an approximate upper limit for an acceptable reaction. As previously indicated, the reaction is strongly exothermic, and in normal circumstances there is considerable danger of explosion. However, and in this invention, the reaction is controlled in the presence of the N-methyl pyrollidone solvent if the maleic anhydride is added slowly to the solution of the amino compound in solution in that solvent.

The monoepoxide which can be reacted with the carboxyl-functional amide produced herein to consume all or part of the carboxyl functionality is subject to wide variation. Propylene oxide is preferred because of its availability and ease of use, but ethylene oxide and butylene oxide as well as esters, like the glycidyl ester of versatic acid (Cardura E), are also useful. Oxides which are unsaturated monoepoxides, like allyl glycidyl ether or glycidyl methacrylate, can be used, but these introduce expense and produce a polyethylenically unsaturated ester which is less preferred.

The reaction with epoxide functionality is also carried out in solvent medium, and this reaction is also well known, being a simple esterification of the carboxyl group in the unsaturated amide to form an hydroxy ester. This esterification proceeds easily at moderate temperature, such as about 70° C., in the presence of a basic catalyst, benzyl trimethylammonium chloride being typical and used in the Examples.

The aqueous emulsion copolymerization of monomers including the hydroxy-functional monoethylenically unsaturated amides of this invention is conventional, and the monomers used in the copolymerization are a matter of common and general knowledge in the paint industry. The emulsion copolymerization is illustrated in the Examples of this application, and suitable monomers are illustrated by acrylate esters (ethyl acrylate and butyl acrylate), methacrylate esters (methyl methacrylate and butyl methacrylate), vinyl acetate, ethylene, dimethyl acrylamide, and the like. These are usually balanced to give a glass transition temperature below about 20° C., usually between −10° C. and +10° C., as is well known in the art of latex paints. The pigmentation of these paints, usually with a pigment like titanium dioxide (rutile), is also conventional.

All proportions herein, including the examples and the claims, are by weight, unless otherwise stated.

EXAMPLE 1

129 grams (1 mole) of aminoethyl ethylene urea and 170 grams of N-methyl pyrollidone are placed in a reactor equipped with a reflux condensor and heated to 120° C. with agitation. A total of 98 grams of maleic anhydride (1 mole) is added slowly in increments over a two hour period, care being taken to avoid any uncontrolled exotherm. After addition of maleic anhydride has been completed, the reactor is held at 120° C. for an additional 2 hours, and then the reactor is cooled to 70° C. to complete the production of a monoethylenically unsaturated amide having carboxyl functionality.

2 grams of benzyl trimethyl ammonium chloride catalyst are then added and then 90 grams of propylene oxide (a stoichiometric excess based on the carboxyl functionality present) are added over a 1 hour period. The reactor is maintained at 70° C. until the acid value is less than 10 which indicates that the carboxyl functionality has been substantially consumed and replaced by hydroxy ester groups.

The product has a solids content of 66.5%, an acid value of 5.9 and a Gardner-Holdt viscosity of T-U.

EXAMPLE 2

An aqueous emulsion copolymer was prepared using 84% of vinyl acetate, 14% of n-butyl acrylate and 2% of the adhesion promoter of Example 1. The polymerization was carried out in conventional fashion using 4.4% of a nonionic surfactant constituted by 40 moles of ethylene oxide adducted with one mole of nonyl phenol, and 0.2% of an anionic surfactant constituted by sodium alkyl aryl polyether sulfonate (Triton X-200 made by Rohm & Haas may be used).

The polymerization was carried out at 53% solids to provide a latex having an average particle size of 0.2 micron. After pigmentation with titanium dioxide, rutile, and testing over a gloss alkyd surface, excellent adhesion was obtained. The emulsion was of excellent quality. Scrub resistance was also excellent.

As a matter of interest, adhesion is normally detrimentally influenced by the elements when the coated substrate is wet for long periods of time. Accordingly, the adhesion which is tested is "wet adhesion" which is the adhesion which is retained after the coated substrate has been immersed in water and then dried.

What is claimed is:

1. A ureido-functional, ethylenically unsaturated copolymerizable monomer which is the adduct formed by reacting an aminoalkyl alkylene urea having the formula:

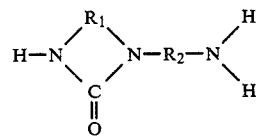

in which $R_1$ is alkylene having 2 or 3 carbon atoms; and $R_2$ is alkylene having 2 to 10 carbon atoms, with a maleic anhydride compound having the formula:

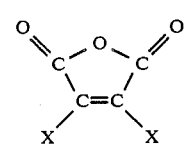

where X is selected from hydrogen, $C_1$-$C_4$ alkyl, and halogen, to form an unsaturated carboxyl-functional amide, the adduction reaction being carried out in solution in N-methyl pyrollidone at a temperature in the range of 80° C. to 130° C.

2. A monomer as recited in claim 1 in which an aminoethyl or aminopropyl ethylene urea is used.

3. A monomer as recited in claim 1 in which maleic anhydride is used in substantially a stoichiometric amount based on the amine functionality present.

* * * * *